United States Patent
Grady

(10) Patent No.: US 8,591,475 B2
(45) Date of Patent: Nov. 26, 2013

(54) CONTROLLED RELEASE STRUCTURE FOR ATTACHING MEDICAL DEVICES

(75) Inventor: William N. Grady, Haledon, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 762 days.

(21) Appl. No.: 11/619,658

(22) Filed: Jan. 4, 2007

(65) Prior Publication Data

US 2007/0185461 A1 Aug. 9, 2007

Related U.S. Application Data

(63) Continuation of application No. 10/428,720, filed on May 2, 2003, now Pat. No. 7,217,258.

(51) Int. Cl.
*A61M 5/00* (2006.01)

(52) U.S. Cl.
USPC .......................................... 604/240

(58) Field of Classification Search
USPC ............ 604/110, 187, 188, 264, 905, 164.07, 604/164.04, 181, 533–539, 240–244
See application file for complete search history.

(56) References Cited

U.S. PATENT DOCUMENTS

| | | |
|---|---|---|
| 791,802 A | 6/1905 | De Lisle |
| 1,524,242 A | 1/1925 | Hein, G. N. |
| 1,591,762 A | 7/1926 | Haines |
| 1,683,349 A | 9/1928 | Hein |
| 1,683,350 A | 9/1928 | Hein |
| 2,020,111 A | 11/1935 | Eisele |
| 2,034,294 A | 3/1936 | Hein |
| 2,088,338 A | 7/1937 | Popper et al. |
| 2,834,346 A | 6/1955 | Adams |
| 2,764,978 A | 10/1956 | Everett |
| 2,828,743 A | 4/1958 | Ashkenaz et al. |
| 2,902,995 A | 9/1959 | Loper |
| 3,043,304 A | 7/1962 | Higgins |
| 3,469,581 A | 9/1969 | Burke |
| 3,472,227 A | 10/1969 | Burke |
| 3,527,217 A | 9/1970 | Gettig |
| 4,040,421 A | 8/1977 | Young |

(Continued)

FOREIGN PATENT DOCUMENTS

| | | |
|---|---|---|
| EP | 1254677 B1 | 12/2005 |
| FR | 567078 | 2/1924 |

(Continued)

OTHER PUBLICATIONS

Encarta.msn.com: definition of 'buckle' http://encarta.msn.com/encnet/features/dictionary/DictionaryResults.aspx?refid=1861593141.*

(Continued)

*Primary Examiner* — Kami A Bosworth
(74) *Attorney, Agent, or Firm* — Servilla Whitney LLC

(57) ABSTRACT

A medical device for use with a fluid transfer device includes a hub having an open proximal end with a frusto-conically-shaped cavity therein, a distal end and a passageway therethrough. The cavity is part of the passageway. A release element in the passageway of the hub is positioned to block fluid-tight engagement of the frusto-conically-shaped tip with the cavity of the hub. Structure is provided to release at least part of the release element, upon application of a proximally directed force on the hub, to allow the abrupt fluid-tight engagement of the tip and the cavity in the hub.

17 Claims, 20 Drawing Sheets

(56) References Cited

U.S. PATENT DOCUMENTS

| | | | |
|---|---|---|---|
| 4,281,653 A | | 8/1981 | Barta et al. |
| 4,430,080 A | | 2/1984 | Pasquini et al. |
| 4,490,142 A | | 12/1984 | Silvern |
| 4,589,871 A | | 5/1986 | Imbert |
| 4,675,020 A | | 6/1987 | Mc Phee |
| 4,747,839 A | | 5/1988 | Tarello et al. |
| 4,822,343 A | | 4/1989 | Beiser |
| 5,047,021 A | | 9/1991 | Utterberg |
| 5,053,015 A | | 10/1991 | Gross |
| 5,066,287 A | | 11/1991 | Ryan |
| 5,312,377 A | | 5/1994 | Dalton |
| 5,348,544 A | | 9/1994 | Sweeney et al. |
| 5,405,340 A | | 4/1995 | Fageol et al. |
| 5,456,675 A | | 10/1995 | Wolbring et al. |
| 5,458,577 A | | 10/1995 | Kishigami |
| 5,458,580 A | | 10/1995 | Hajishoreh |
| 5,466,223 A | * | 11/1995 | Bressler et al. ............... 604/110 |
| 5,535,771 A | | 7/1996 | Purdy et al. |
| 5,637,101 A | | 6/1997 | Shillington |
| 5,681,295 A | | 10/1997 | Gyure et al. |
| 5,713,876 A | | 2/1998 | Bogert et al. |
| 5,733,265 A | | 3/1998 | Bachman et al. |
| 5,772,643 A | | 6/1998 | Howell et al. |
| 5,810,768 A | | 9/1998 | Lopez |
| 5,830,189 A | * | 11/1998 | Chang ..................... 604/164.07 |
| 5,836,919 A | | 11/1998 | Skurka et al. |
| 5,851,201 A | | 12/1998 | Ritger et al. |
| 5,913,846 A | * | 6/1999 | Szabo ........................... 604/263 |
| 5,925,020 A | * | 7/1999 | Nestell .......................... 604/198 |
| 6,132,402 A | | 10/2000 | Tessmann et al. |
| 6,217,560 B1 | | 4/2001 | Ritger et al. |
| 6,436,076 B1 | | 8/2002 | Hsu |
| 6,629,774 B1 | | 10/2003 | Guruendeman |
| 6,706,022 B1 | | 3/2004 | Leinsing et al. |
| 7,115,114 B2 | | 10/2006 | Caizza |
| 7,217,258 B2 | | 5/2007 | Caizza |
| 2002/0138045 A1 | | 9/2002 | Moen |
| 2007/0173776 A1 | | 7/2007 | Caizza et al. |

FOREIGN PATENT DOCUMENTS

| | | |
|---|---|---|
| GB | 1574187 | 9/1980 |
| JP | 53-5891 | 1/1978 |
| JP | 59-2750 | 1/1984 |
| JP | 3-31444 | 3/1991 |
| JP | 7-31679 | 3/1995 |
| JP | 7-303697 | 11/1995 |
| JP | 08-000732 | 1/1996 |
| JP | 8-57058 | 3/1996 |
| JP | 10-113392 | 5/1998 |
| JP | 11-507275 | 6/1999 |
| JP | 2003-505158 | 2/2003 |
| JP | 2003-88587 | 3/2003 |

OTHER PUBLICATIONS

Non-Final Office Action dated Apr. 15, 2009, 13 pgs.

* cited by examiner

CONTROLLED RELEASE STRUCTURE FOR ATTACHING MEDICAL DEVICES

RELATED APPLICATIONS

This application is a continuation of U.S. patent application Ser. No. 10/428,720, filed May 2, 2003, now U.S. Pat. No. 7,217,258, issued May 15, 2007.

FIELD OF THE INVENTION

The present invention relates to a medical device such as a hypodermic needle assembly which is adapted to releasably engage a fluid transfer device such as a syringe. In particular, the present invention relates to a medical device having a releasable element for controlling the minimum force needed to connect a medical device to a fluid delivery device such as a needle assembly and a syringe.

BACKGROUND

A hypodermic syringe consists of a cylindrical barrel, most commonly made of thermoplastic material or glass, with a distal end adapted to be connected to a hypodermic needle assembly or other medical device and a proximal end adapted to receive a stopper and plunger rod assembly. The stopper provides fluid-tight seal between itself and the syringe barrel so that movement of the stopper up and down the barrel will cause liquid, blood or other fluids to be drawn into or forced out of the syringe barrel through the distal end. The stopper is moved along the syringe barrel by applying axial force on a rigid plunger rod which is connected to the stopper and is sufficiently long to be accessible outside of the barrel. The stopper and the plunger rod can be integrally formed of one material such as thermoplastic.

Hypodermic needle assemblies, typically including a cannula and a hub, are often removably attached to syringes for performing a variety of tasks such as the delivery of medication into patients and into devices, and for withdrawing fluid samples from patients and from fluid sources. Usually, the hub of the hypodermic needle assembly has tapered interior surface adapted to engage the tapered tip of the syringe barrel so that the two components are joined in a frictional interference fit. The tapered syringe tip and the complementarily tapered receptacle in the hub are referred to as standard luer fittings. A wide variety of other medical devices such as stopcocks and tubing sets have standard luer fittings which allow them to be engaged to a syringe tip.

It is important that the frictional fit between the syringe tip and the needle hub or other medical device is strong enough to prevent accidental disengagement caused by the fluid pressures within the syringe and/or other factors such as forces applied to the needle hub when actuating safety needle shields connected to the hub. If the syringe tip becomes disengaged from the needle assembly, medication, blood or other fluids will be lost, and there is also potential for contamination.

The prior art teaches many structures for improving the connection between medical devices having tapered luer fittings such as needle assemblies and syringes. These structures include complementary engaging structure on both the needle hub and syringe barrel tip such as projections and recesses providing for a snap-fit arrangement. Manually releasable locking structures have been provided to increase the connection between the needle hub and barrel tip while allowing reasonable forces for disconnection of these components. Also, enhancements to the luer tip of the syringe barrel such as coatings, sandblasting and mechanical collars have provided for improved connection between a needle hub and a syringe barrel tip. Many of the structures taught by the prior art do not contemplate the subsequent removal of the needle assembly from the syringe barrel. Others require extensively modified needle hubs and barrel tips. Structures having a tapered luer fitting such as a needle assembly and syringe barrel are adequate for normal use when the needle assembly is properly installed on the syringe tip. Difficulties can arise if the user does not use enough force to frictionally engage the luer tapered surfaces which can result in inadvertent disconnection of the needle assembly.

Although the prior art teaches various devices and structures for improving the strength of the connection between a syringe barrel and the hub of a needle assembly or other fluid handling device, there is still a need for a simple, straight-forward, reliable needle hub or other fluid-handling device having structure which improves the strength of the connection with the syringe tip or other device having a standard tapered luer tip by requiring a minimum force of engagement.

SUMMARY OF THE INVENTION

A medical device for use with a fluid transfer device having a frusto-conically shaped tip includes a hub having an open proximal end with a frusto-conically-shaped cavity therein, a distal end and a passageway therethrough. The cavity is part of the passageway. A release element is positioned in the passageway of the hub to block fluid-tight engagement of the frusto-conically shaped tip with the cavity of the hub. Structure is provided for releasing at least part of the release element, upon application of a proximally directed force on the hub, to allow the abrupt fluid-tight engagement of the tip and the cavity in the hub. The abrupt transition to fluid-tight engagement can provide a tactile and audible indication to the user that the hub and the tip are properly engaged.

The medical device of the present invention may also include a needle cannula having an open proximal end, a distal end and a lumen therethrough. The proximal end of the needle cannula is joined to the distal end of the hub so that the lumen is in fluid communication with the passageway in the hub.

The proximally directed force on the hub is desirably greater than 0.5 kg. and preferably between 1 kg. and 5 kg.

The structure for allowing the release of part of the release element may include a discontinuity on the release element or the hub engaging a complementary discontinuity on the hub or the release element. The discontinuities are configured to disengage upon the application of the proximally directed force on the hub. The hub may include a proximally directed hollow extension in the passageway having a discontinuity thereon and configured to allow fluid flow through the passageway. The release element includes a complementary discontinuity thereon engages the discontinuity and is positioned so that upon disengagement in response to the proximally-directed force, at least part of the release element moves distally into the space around the extension. The release element is configured to allow fluid flow through the passageway.

An alternative release element includes a proximal end and a distal end capable of telescoping action with respect to each other. The structure for releasing includes at least one frangible link between the proximal and distal end of the release element. The link is breakable upon application of the proximally-directed force on the hub so that the proximal and distal ends of the release element can telescope with respect to each other and allow engagement of the tip and the hub. Adhesive may be used as a frangible structure to allow the release of part or all of the release element in various embodiments.

Another alternative release element includes a distal end positioned in the passageway in the hub and a proximal end including a proximally directed axial beam. The beam has a free end adapted to contact the distal end of the frusto-conically-shaped tip to block fluid-tight engagement of the tip and the hub. The beam is configured to buckle upon application of the proximally directed force on the hub.

Another alternative embodiment of the needle assembly of the present invention further includes a guide element on the hub having an aperture therethrough. An elongate barrier arm having a proximal end and a distal end is positioned in the aperture for sliding axial movement therein. The distal end of the barrier arm includes a barrier element having a distal end, a proximal end and a needle passageway therethrough. The needle cannula is positioned at least partially within the needle passageway of the barrier element. The barrier arm is movable from at least a first retracted position wherein the distal end of the needle cannula passes completely through the barrier element so that the distal end of the needle cannula is exposed, to a second extended position wherein the barrier element surrounds the distal end of the needle cannula to prevent incidental contact with the distal end of the needle cannula. A finger contact surface on the barrier arm is provided to accept digital force to the barrier arm to move the barrier arm into the second extended position.

Still another alternative embodiment of the needle assembly of the present invention further includes a needle guard having a proximal end, a distal end and a needle passageway therethrough. The needle guard is movable along the needle cannula from a first position substantially adjacent the proximal end of the needle cannula to a second position where a distal tip of the needle cannula is intermediate the opposed proximal and distal ends of the needle guard. A hinged arm having proximal and distal segments articulated to one another for movement between a first position wherein the segments are substantially collapsed onto one another and a second position where the segments are extended from one another is provided. The proximal segment of the hinged arm is articulated to a portion of the hub. The distal segment of the hinged arm is articulated to the needle guard. The proximal and distal segments of the hinged arm have respective lengths for permitting the guard to move from the first position to the second position on the needle cannula and for preventing the guard from moving distally beyond the second position. The components of the hinged arm may be integrally molded of thermoplastic material.

All embodiments of the present invention may include a needle cannula and a pivotable needle shield having a cavity therein hingedly connected to the hub and capable of pivoting from a needle exposing position, which allows access to the distal end of the needle cannula, and a needle protecting position wherein the distal end of the needle cannula is within the cavity of the needle shield.

DETAILED DESCRIPTION

Figure 1:
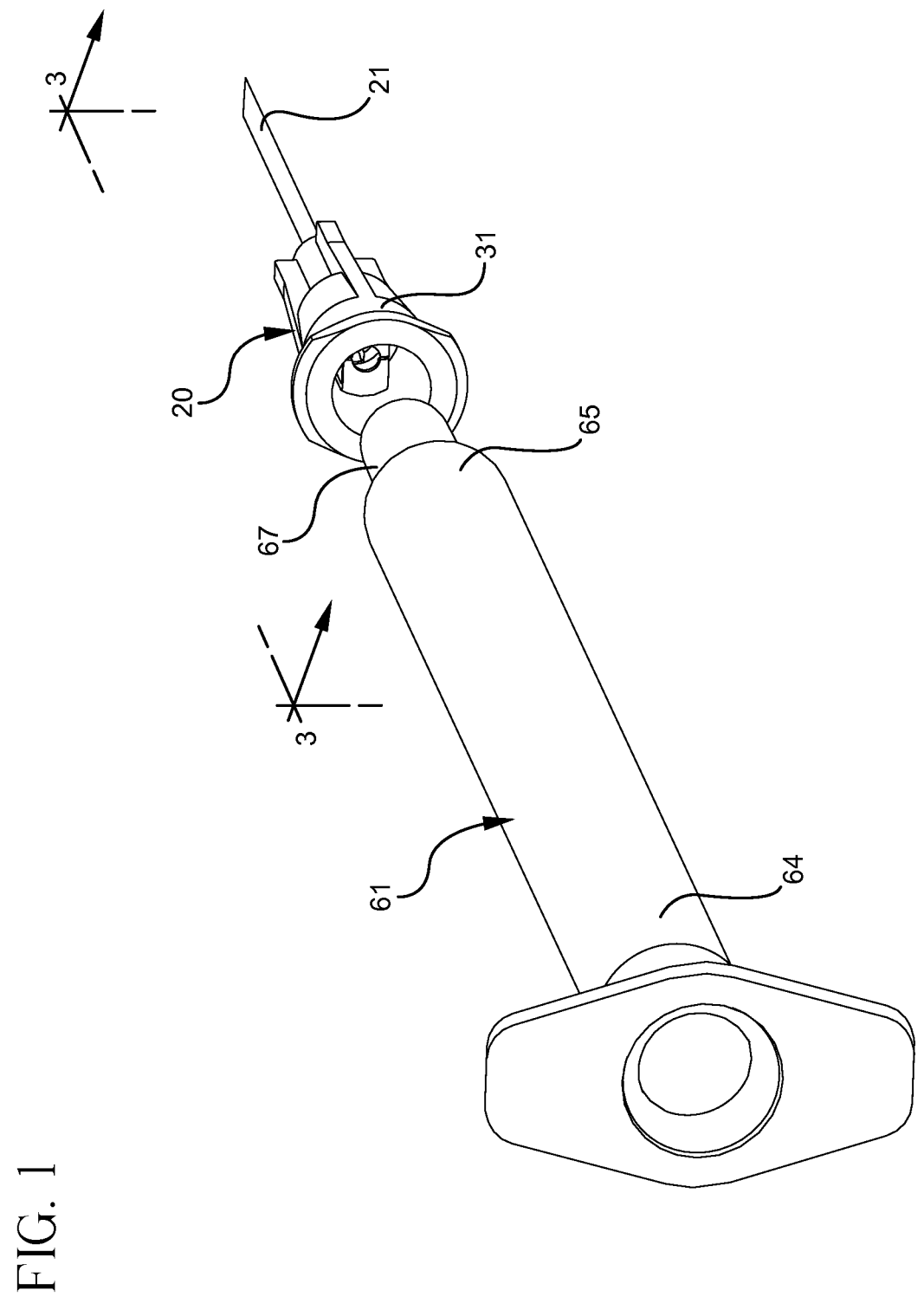
FIG. 1 is a perspective exploded view illustrating a needle assembly of the present invention and a syringe barrel.
Figure 2:
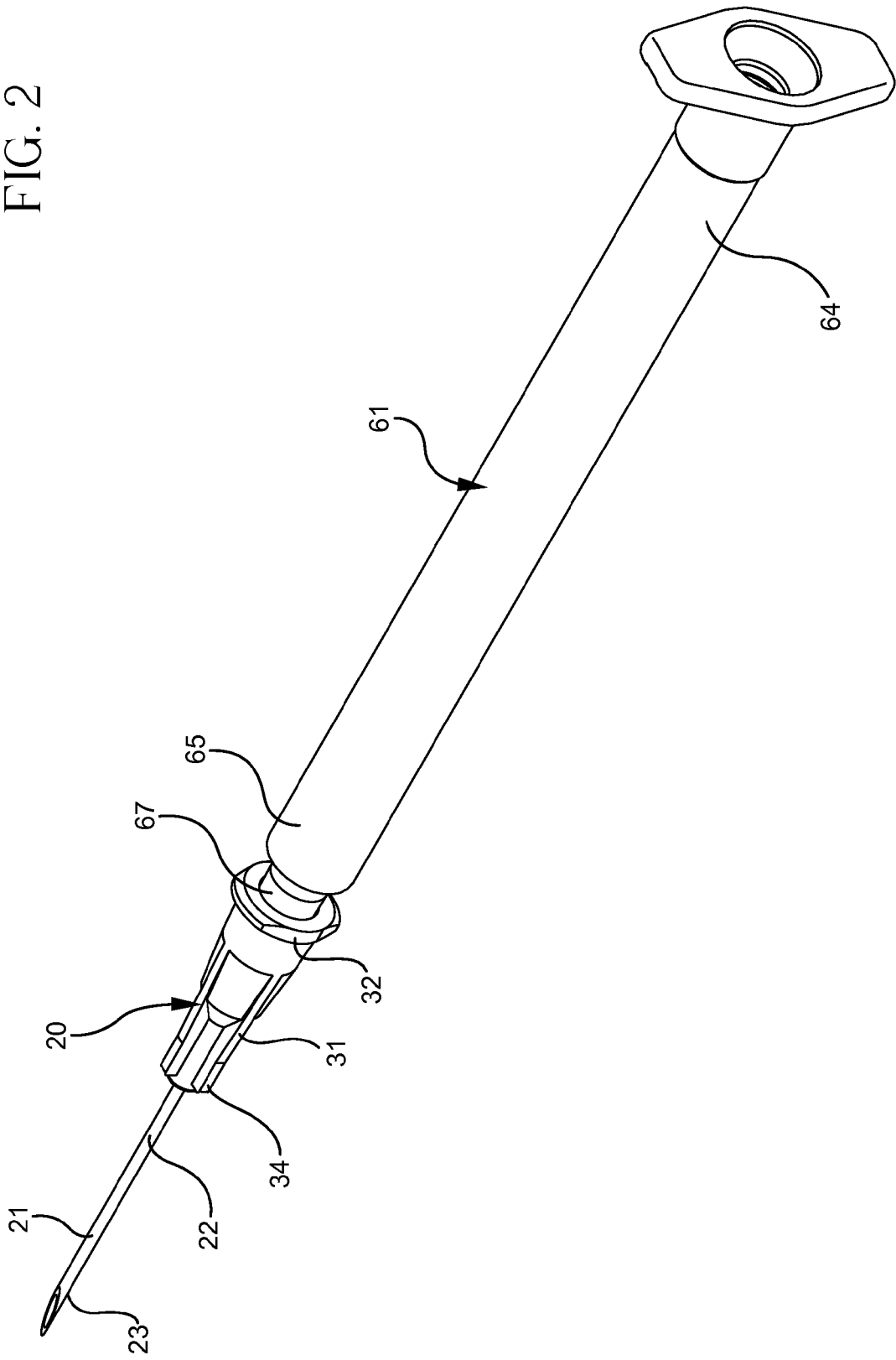
FIG. 2 is a perspective view of the needle assembly of FIG. 1 connected to the syringe barrel.
Figure 3:
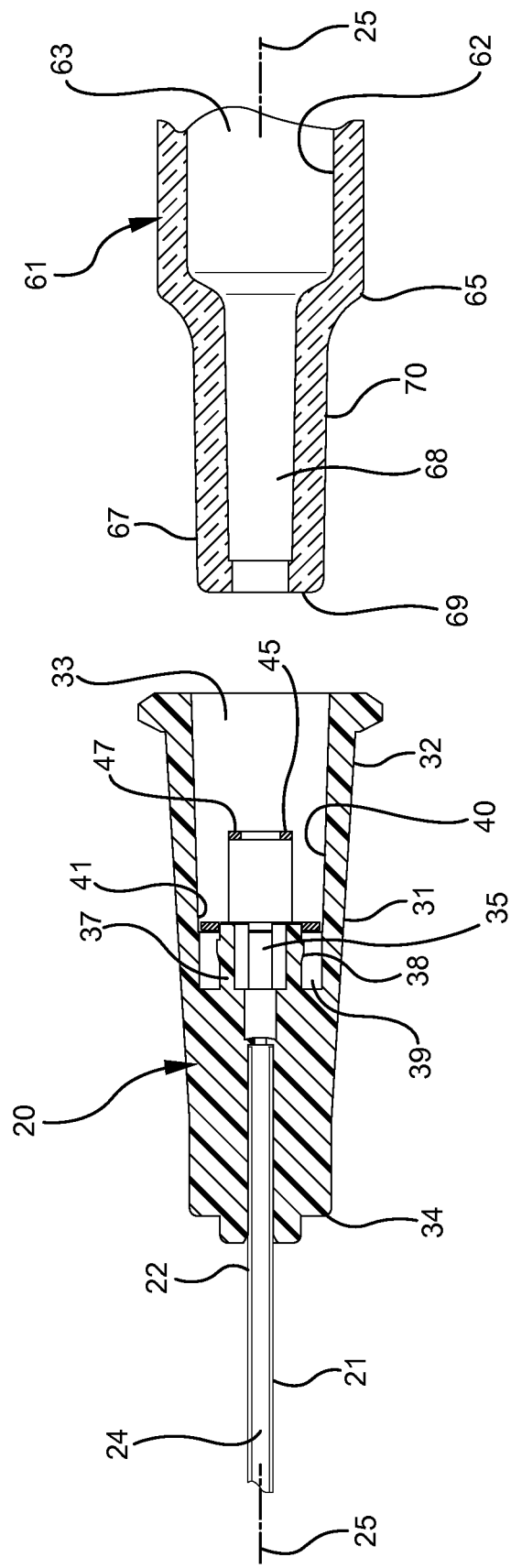
FIG. 3 is an enlarged partial cross-sectional view of the needle assembly and syringe barrel of FIG. 1 taken along line 3-3.
Figure 4:
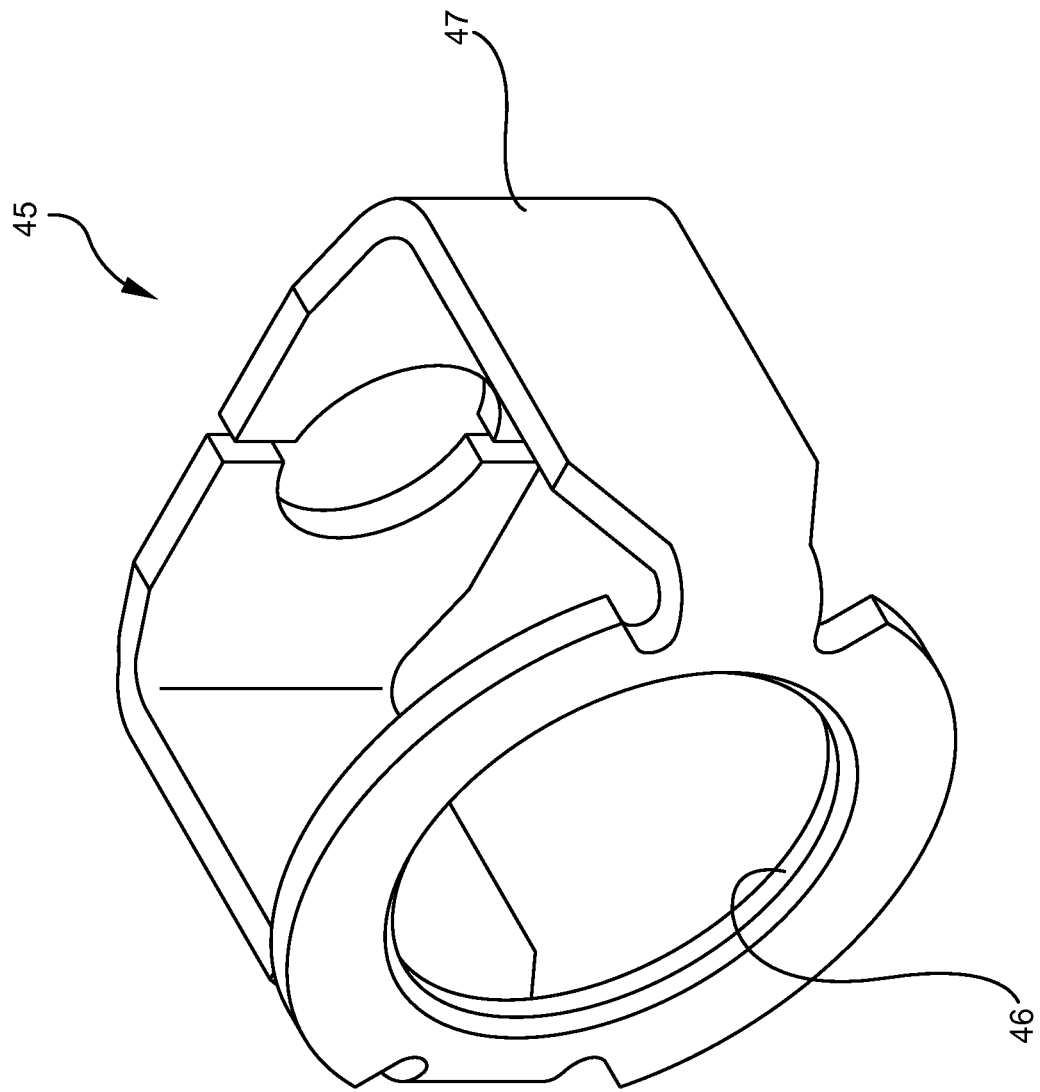
FIG. 4 is a perspective view of the release element of the needle assembly.
Figure 5:
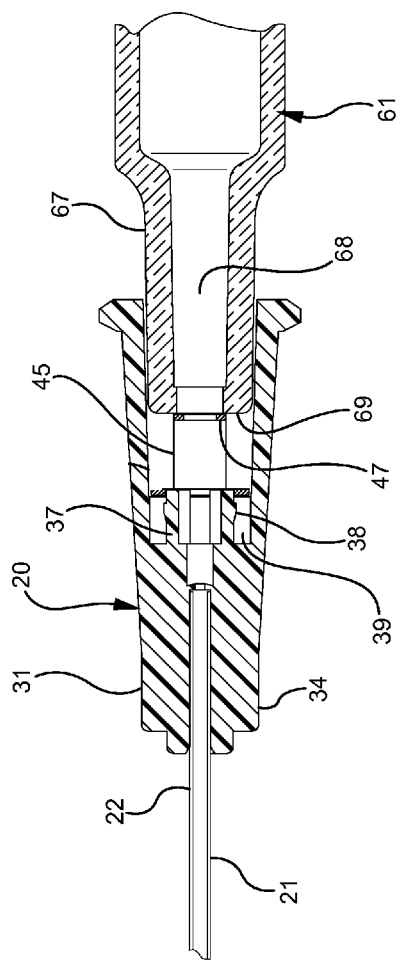
FIG. 5 is an enlarged partial cross-sectional view of the needle assembly and syringe barrel illustrating the position of the release element before hub and barrel tip engagement.
Figure 6:
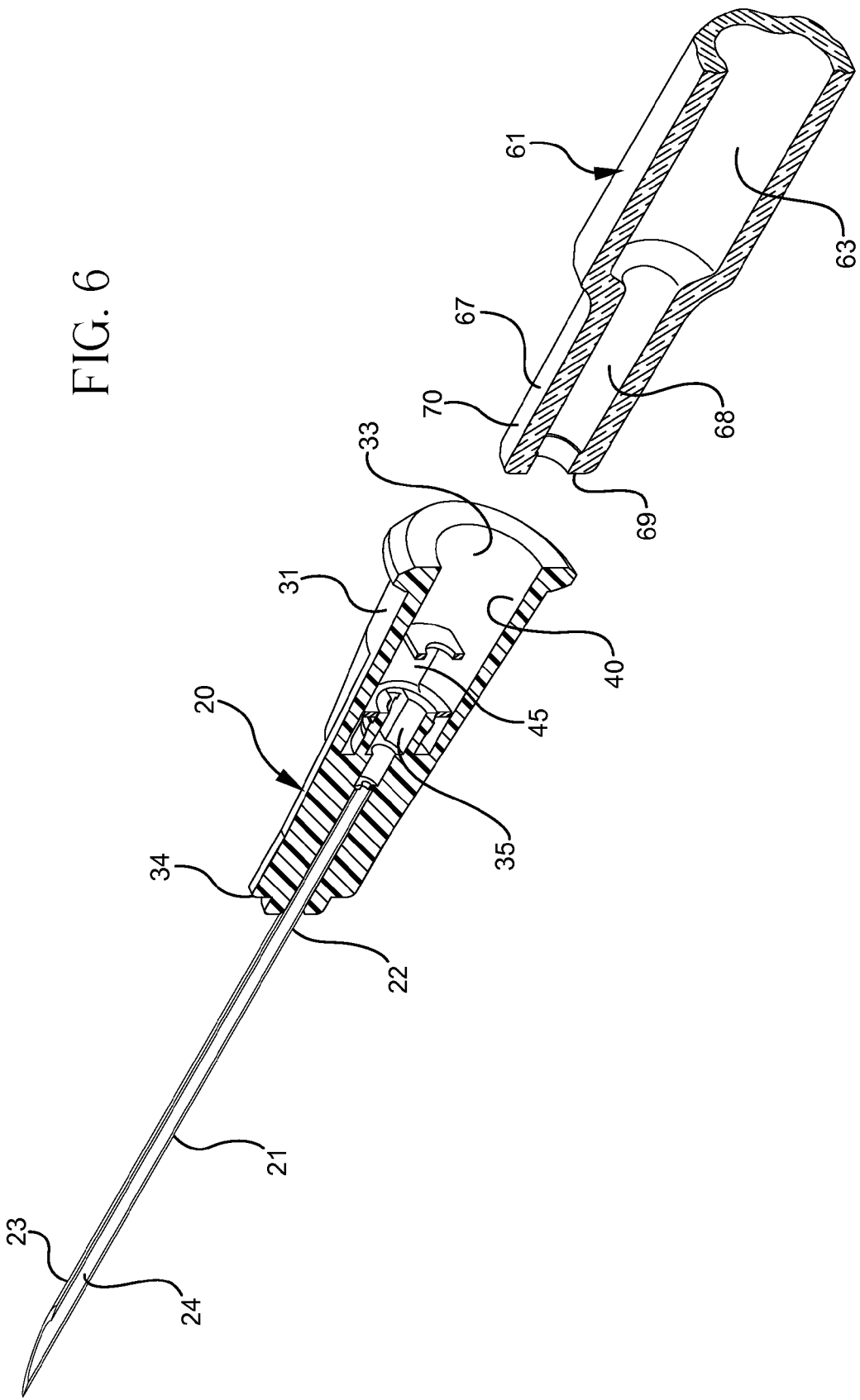
FIG. 6 is a perspective partial cross-sectional view of the needle assembly and the syringe barrel tip similar to FIG. 3.

While this invention is satisfied by embodiments in many different forms, there are shown in the drawings and will herein be described in detail, preferred embodiments of the invention with the understanding that the present disclosure is to be considered exemplary of the principles of the invention and not intended to limit the invention to the embodiments illustrated. The scope of the invention will be measured by the appended claims and their equivalents.

Referring to FIGS. 1-7, a medical device such as needle assembly 20 includes a needle cannula 21 having a proximal end 22, a distal end 23 and a lumen 24 therethrough defining a longitudinal axis 25. A hub 31 includes an open proximal end 32 with a cavity 33 therein, a distal end 34 and a passageway 35 therethrough. The cavity is part of the passageway. The proximal end of the needle cannula is joined to the distal end of the hub so that the lumen of the needle cannula is in fluid communication with the passageway of the hub.

Needle cannula 21 is preferably made of metal such as stainless steel and can be held to the hub using various manufacturing methods with adhesives such as epoxy being preferred. The hub is preferably made of injection moldable plastic such as polypropylene, polyethylene, polycarbonate and combinations thereof. The needle cannula and hub may be integrally formed of thermoplastic material. The needle assembly can be used with a variety of fluid transfer devices having a frusto-conically shaped luer tip such as a hypodermic syringe.

A syringe includes syringe barrel 61 having a inside surface 62 defining a chamber 63, an open proximal end 64, and a distal end 65 including an elongate frusto-conically shaped tip 67 having a conduit 68 therethrough. The needle assembly is connected to the syringe barrel so that the frusto-conically shaped tip is in fluid-tight engagement with the frusto-conically shaped cavity in the hub and the lumen is in fluid communication with the cavity. A concern with prior art needle assemblies and syringe barrels having complementary luer fittings is that the needle assembly may become loosened or disengaged from the syringe tip during use. This may happen because the user does not apply enough axial force to properly engage the needle hub to the barrel tip, and the hydraulic pressure of the injection process and/or forces induced during normal use dislodge the needle assembly from the barrel.

Figure 7:
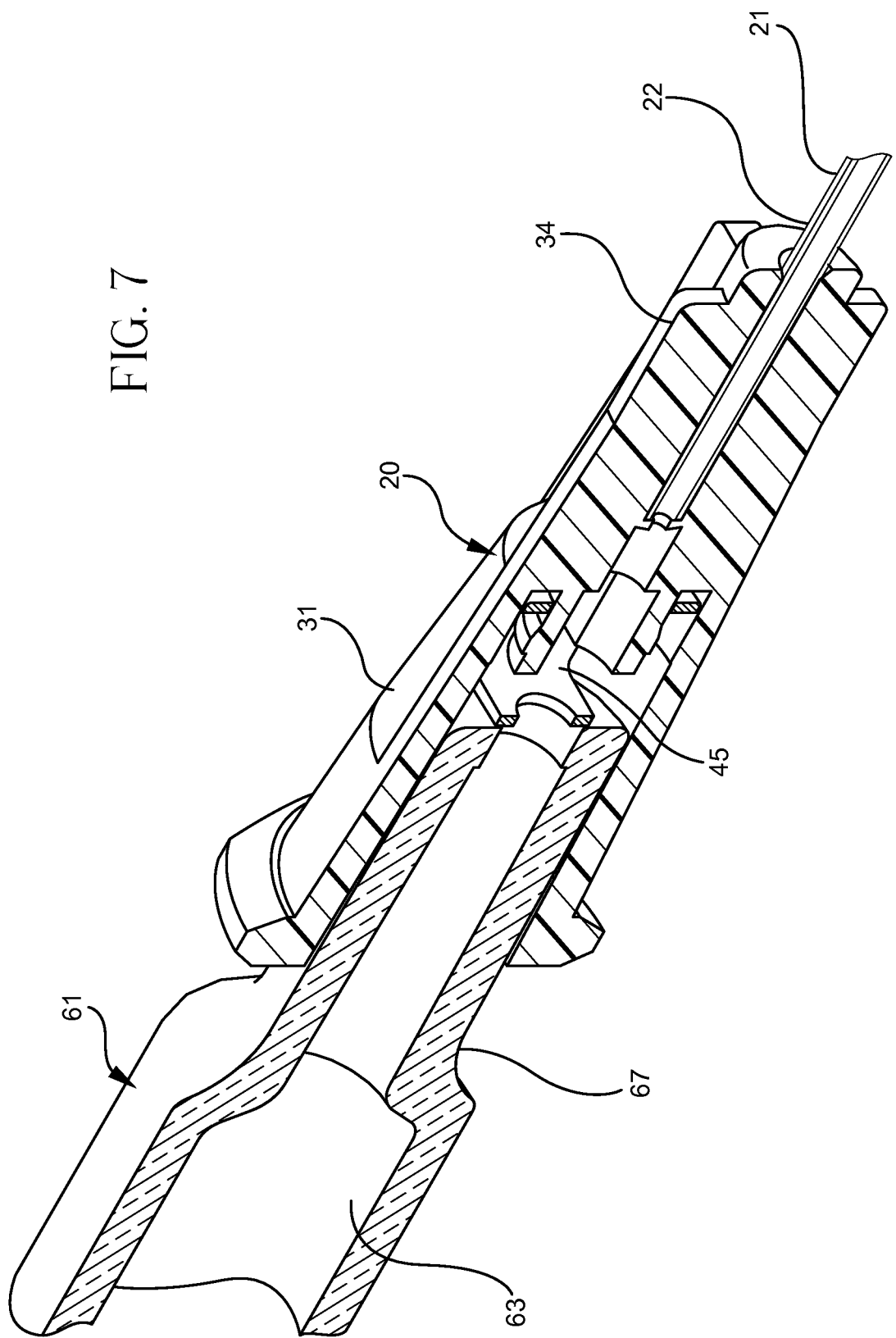
FIG. 7 is a partial cross-sectional perspective view illustrating the needle assembly frictionally engaged to a syringe barrel.

The present invention provides a medical device having a fluid transfer fitting, such as a needle hub, which can be used with any standard luer slip fitting to provide improved retention of the needle assembly to the luer slip fitting and to allow for more uniform installation force as will be explained in detail hereinafter. This improvement is accomplished through the use of a release element such as release element 45 in the passageway of the hub. Release element 45 is positioned to block fluid-tight engagement of the frusto-conically shaped tip of the syringe barrel with the cavity of the hub. In this embodiment the release element is positioned in a distal end 41 of cavity 33. Means for releasing at least part of the release element, upon application of a proximally directed force on the hub, to allow the abrupt fluid-tight engagement of the tip and the cavity in the hub is provided. In this embodiment, means for releasing includes a discontinuity on the release element or the hub engaging a complementary discontinuity on the other of the release element or the hub. Discontinuities are configured to disengage upon the application of a proximally directed force on the hub. In this embodiment, the hub includes a proximally directed hollow extension 37 in the passageway having a discontinuity in the form of radial projection 38 thereon. Hollow extension 37 is configured to allow fluid flow through the passageway and defines an annular space 39. Release element 45 contains a complementary discontinuity in the form of inwardly directed edge 46 thereon. Radial projection 38 and inwardly directed edge 46 are configured to release when a pre-determined proximally-directed force used to engage the cavity of the hub on the tip of the barrel is applied. Specifically, the force between proximal end 47 of the release element and a distal end 69 of tip 67 will cause radial projection 38 of the hub to disengage inwardly directed edge 46 of the release element allowing the release element to move forward so that at least a portion of the release element is in annular space 39 of the hub. The relatively abrupt release of the release element allows the cavity of the hub to engage the tip of the syringe barrel with sufficient force to provide an adequate frictional interference fit between an inside surface 40 of cavity 33 and an outside surface 70 of tip 67, as best illustrated in FIG. 7. An important advantage of the present invention is that the release element and the hub can be configured to provide an audible click when the hub engages the tip of the barrel and/or to maximize the tactile feeling when engagement occurs to give the user positive feedback that the needle assembly is properly engaged to the syringe barrel tip.

An important advantage of the present invention is that it will not allow a frictional fluid-tight engagement between the tip of the syringe barrel and the cavity in the hub until a pre-determined force which can provide a generally adequate frictional interference fit between the hub and the syringe tip is reached. This feature eliminates the ability of the user to connect the hub to the syringe barrel using less than a predetermined force needed to provide a frictional interference fit that will usually be strong enough to maintain itself during normal use of the medical device. This important advantage can be achieved when using the present invention with standard luer slip tips on syringe barrels and other fluid delivery devices without the need to modify the luer tip.

The discontinuities and complementary discontinuities on the release element and the hub can encompass a wide variety of structures including projections and recesses either singular or multiple to produce a snap-fit arrangement or overlapping dimensions to produce a press-fit relationship between the release element and the hub and variations thereof wherein the release element must overcome a physical engagement with the hub to release therefrom. Means for releasing as used herein is intended to include the structures described above and other means such as adhesives or frangible connections between the release element and the hub which break or disconnect upon application of the desired force. Means for releasing may also include an additional element between the release element and the hub. All these variations fall within the purview of the present invention, and the interference or snap-fit relationship of the retaining element to the hub illustrated in FIGS. 1-7 is merely representative of these many possibilities.

The release element is made of sheet metal such as stainless steel but can be fabricated in a wide variety of materials and configurations that will allow it to perform its function to release upon the application of the desired force. The desired force may vary based on the materials used to construct the hub and the surface finish of the cavity. For most applications involving plastic tips on standard luer tip syringes and other fluid transfer devices, a proximally directed force of equal or greater than 0.5 kg (1.1 pounds) is desired to cause the release of the release element. A release under a proximally directed force of between 1 kg and 5 kg (2.2 pounds and 11 pounds) is preferred.

In use, as best illustrated in FIGS. 3 and 5-7, needle assembly 20 is connected to syringe barrel 61 by placing the elongate frusto-conically shaped barrel tip into the frusto-conically-shaped cavity of the needle hub until distal end 69 of tip 67 contacts proximal end 47 of release element 45 and applying an axial force sufficient to release the release element and allow the abrupt fluid-tight engagement of the tip and the cavity in the hub as illustrated in FIG. 7. During installation, all or part of the release element moves distally in the hub cavity to allow engagement of the barrel tip and the hub cavity.

Figure 8:
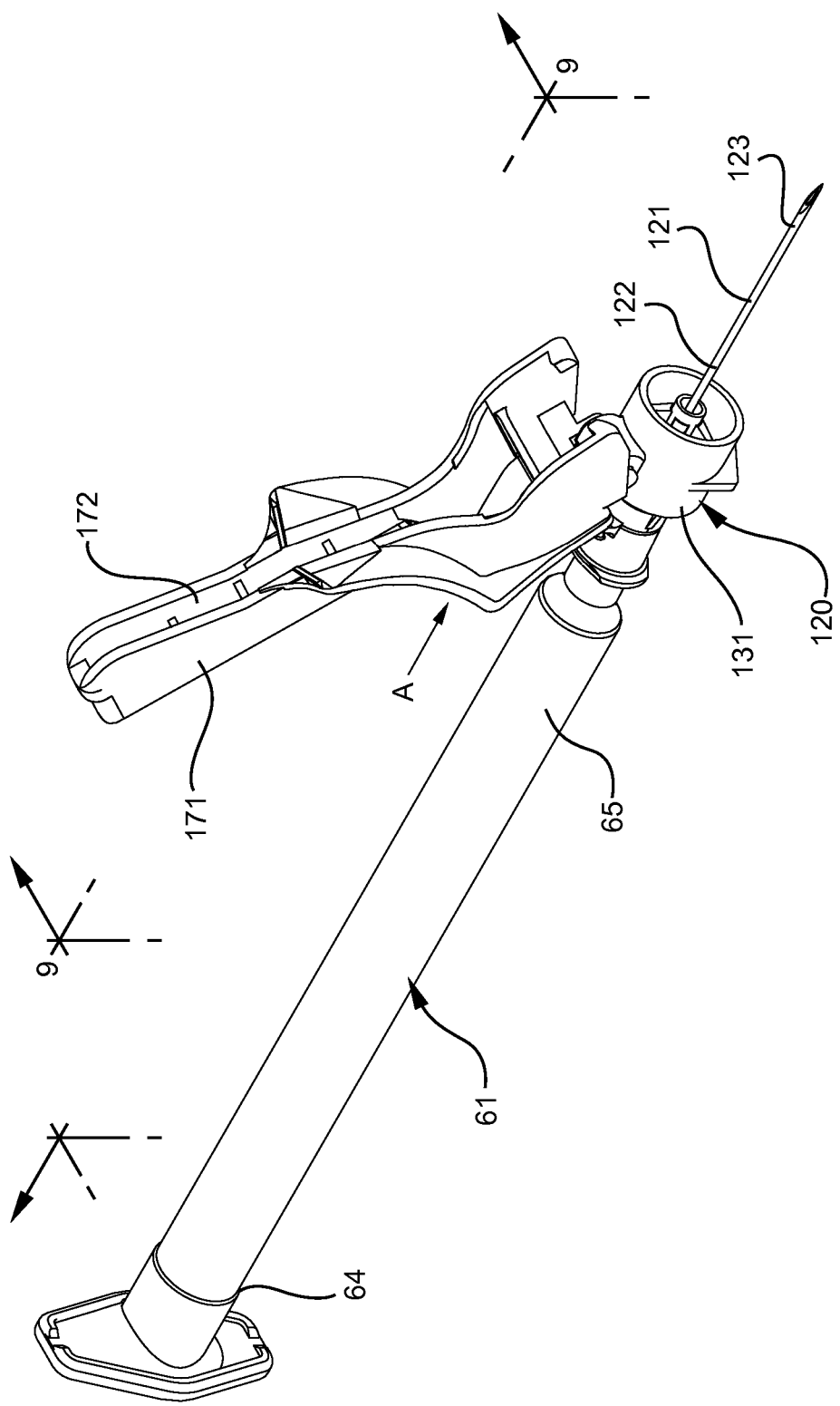
FIG. 8 is a perspective view of a syringe barrel and an alternative needle assembly having a rotatable needle shield.
Figure 9:
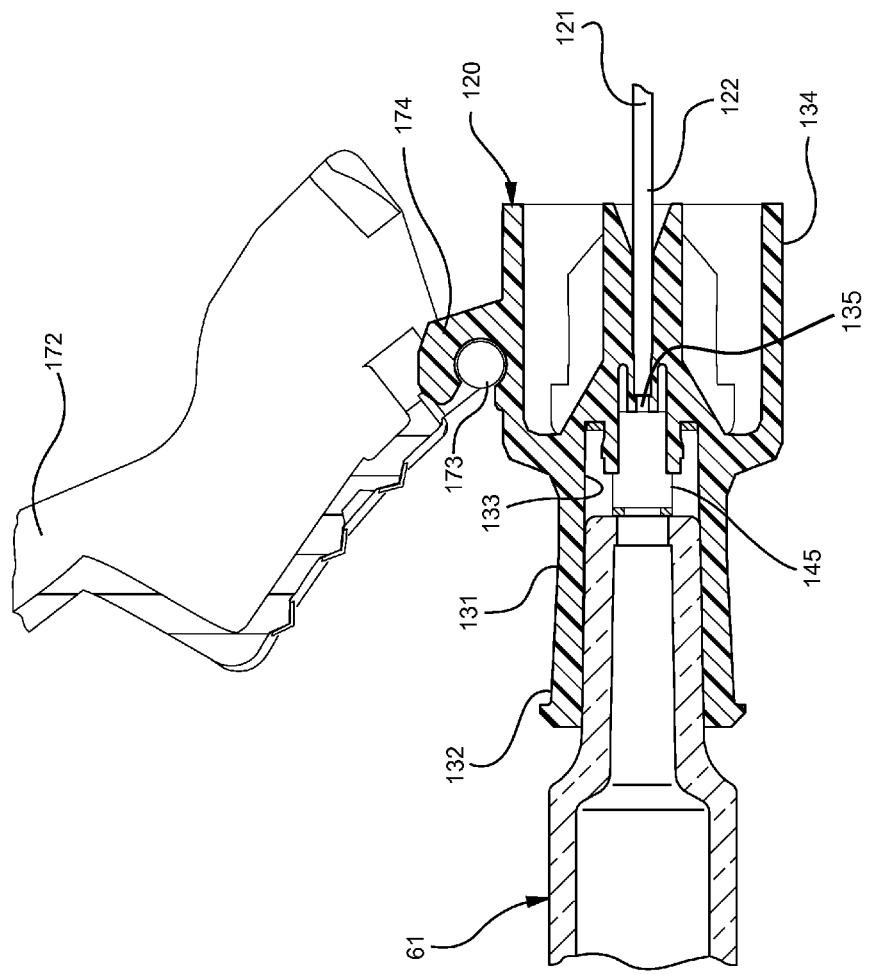
FIG. 9 is an enlarged cross-sectional view of the syringe barrel and needle assembly of FIG. 8 taken along line 9-9.

FIGS. 8-9 illustrate an alternative embodiment of the needle assembly of the present invention. In this embodiment, needle assembly 120 includes a needle cannula 121 having a proximal end 122, a distal end 123 and a hub 131. Hub 131 includes an open proximal end 132 with a frusto-conically shaped cavity 133, a distal end 134 and a passageway 135 therethrough. The cavity is part of the passageway. The proximal end of the needle cannula is joined to the distal end of the hub so that the lumen of the needle cannula is in fluid communication with the passageway. A release element 145 is in the passageway of the hub positioned to block fluid-tight engagement of the frusto-conically shaped tip with the cavity of the hub until all or part of the release element is displaced distally in the passageway by action of force applied to the release element by the distal end of the syringe barrel tip as illustrated in FIG. 9. Release element 145 functions in a similar manner as release element 45 in the embodiment of FIGS. 1-7. Hub 131 further includes a pivotable needle shield 171 which is hingedly connected to the hub and capable of pivoting from a needle exposing position, as illustrated in FIGS. 8-9, which allows access to the distal end of the needle cannula and a needle protecting position wherein the distal end of the needle cannula is within cavity 172 of the needle shield. A structure used to provide the pivotable relationship between the hub and the needle shield can include a variety of hinges, linkages, living hinges and the like. In this embodiment, axel 173 on the needle shield engages axel housing 174 on the hub to provide the pivotable relationship.

After use, the user pivots the needle shield into the needle protecting position by applying a digital force to the needle shield. Such a force has at least a component in direction A as illustrated in FIG. 8. The present invention is especially useful as a hinged needle shield needle assembly. Force A is another force which may contribute to the unintentional disconnection of the needle assembly from the syringe barrel which is resisted by the frictional interference fit of a properly installed hub.

Figure 11:
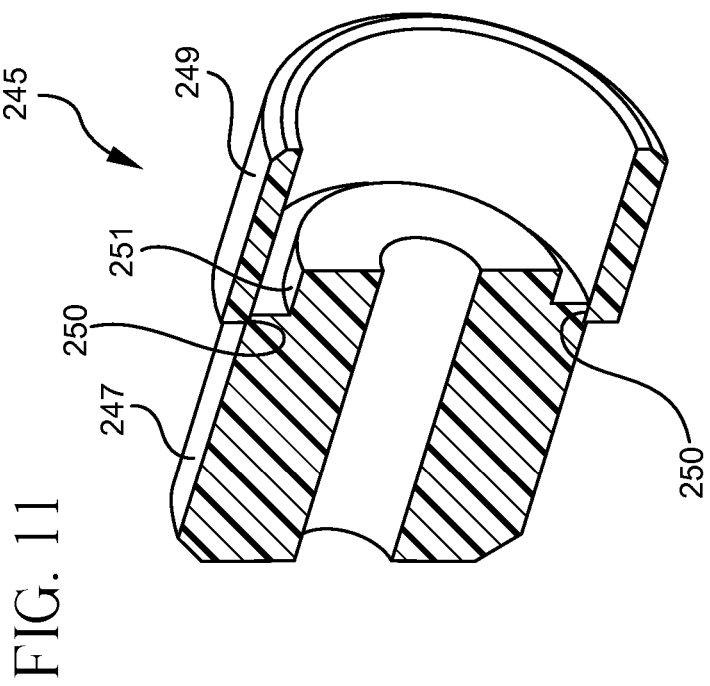
FIG. 11 is a perspective cross-sectional view of the release element of FIG. 10 taken along line 11-11.
Figure 10:
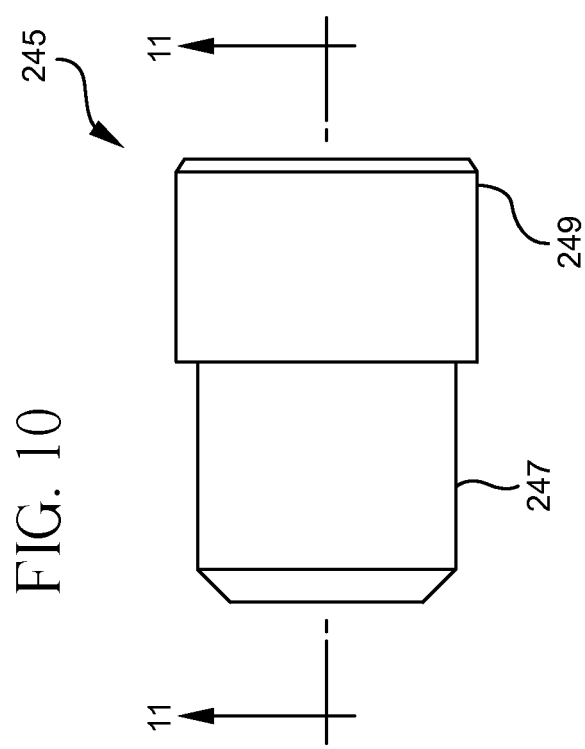
FIG. 10 is an alternative release element of the present invention.
Figure 12:
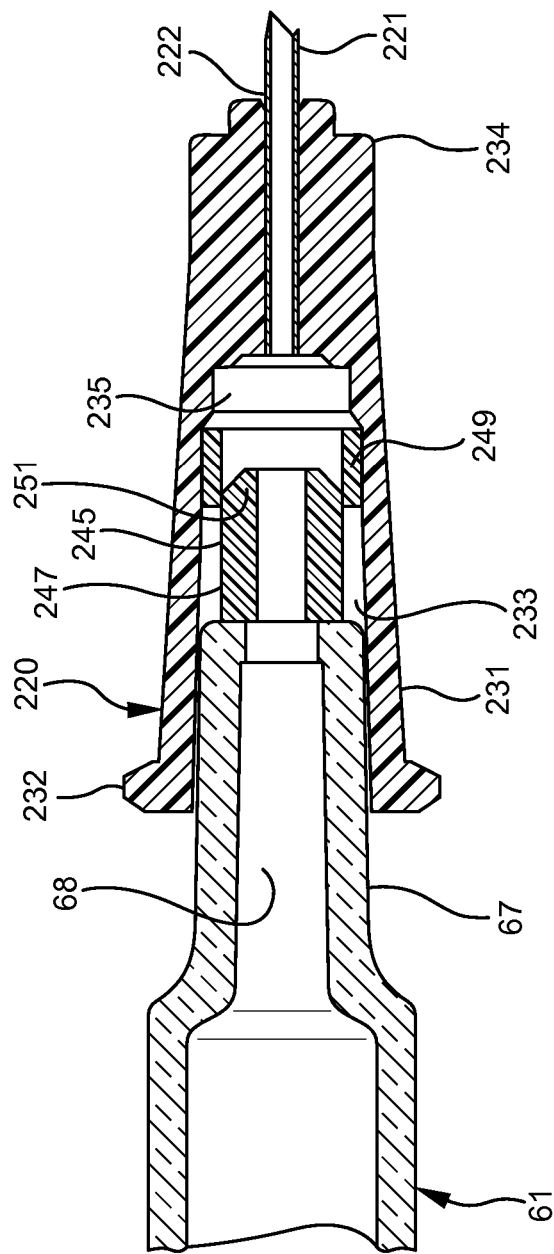
FIG. 12 illustrates a needle assembly having the release element of FIG. 10 and the syringe barrel before frictional engagement of the barrel tip and the hub.
Figure 13:
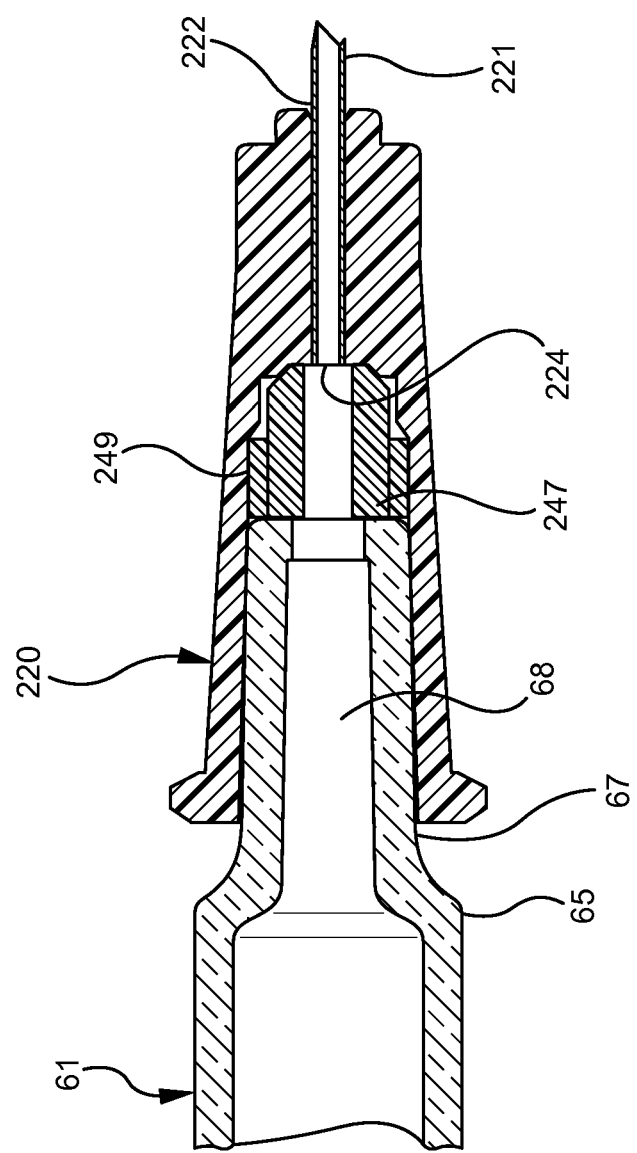
FIG. 13 is a partial cross-section side elevation view of the needle assembly of FIG. 12 frictionally engaged to the syringe barrel tip.

FIGS. 10-12 illustrate an alternative embodiment of the medical device of the present invention. In this embodiment, a needle assembly 220 includes a needle cannula 221 having a proximal end 222, a distal end and a lumen 224 therethrough. A hub 231 includes an open proximal end 232 with a cavity 233 therein, a distal end 234 and a passageway 235 therethrough. The cavity is part of the passageway. The proximal end of the needle cannula is joined to the distal end of the hub so that the lumen of the needle cannula is in fluid communication with the passageway of the hub. Needle assembly 220 is illustrated with a syringe barrel 61 having a distal end 65 including an elongate frusto-conically-shaped tip 57 having a conduit 58 therethrough. As with the embodiment of FIGS. 1-7, the present embodiment includes a release element 245 in the passageway of the hub, positioned to block fluid-tight engagement of the frusto-conically-shaped tip with the cavity in the hub, as best illustrated in FIG. 12. Release element 245 includes a proximal end 247 and a distal end 249 capable of telescoping action with respect to each other. In this embodiment, means for releasing includes at least one frangible link 250 between the proximal end and the distal end of the release element. The frangible link is breakable upon application of a proximally-directed force on the hub so that the proximal end distal ends of the release element can telescope with respect to each other to allow engagement of the syringe barrel tip and the needle assembly hub as best illustrated in FIG. 13. The proximal portion of the release element further includes a distally directed aligning projection 251 which extends into the interior of the distal portion of the release element. The aligning projection is intended to align and center the distal portion with respect to the proximal portion, after frangible link 250 has broken, to help ensure smooth telescoping action between the two elements. There should be at least one frangible link in the release element with a plurality of frangible links being preferred. It is also preferred that the distal end of the release element has an opening therein large enough to accept at least part of the proximal end of the release element when the frangible link is broken. The release element of the present embodiment preferably is cylindrically-shaped with one end of the release element having an outside diameter which is smaller than the inside diameter of the other end of the release element. The frangible link extends between the inside diameter and the outside diameter. The frangible link is preferably integrally formed with the proximal and distal ends of the release element. Adhesives and thermoplastic elastomers may also be used to form a frangible link along with other disengageable structures between the proximal and distal portions all of which are within the purview of the present invention. The integrally formed frangible link illustrated is merely representative of one of these many possibilities, all of which are within the purview of the present invention.

Figure 14:
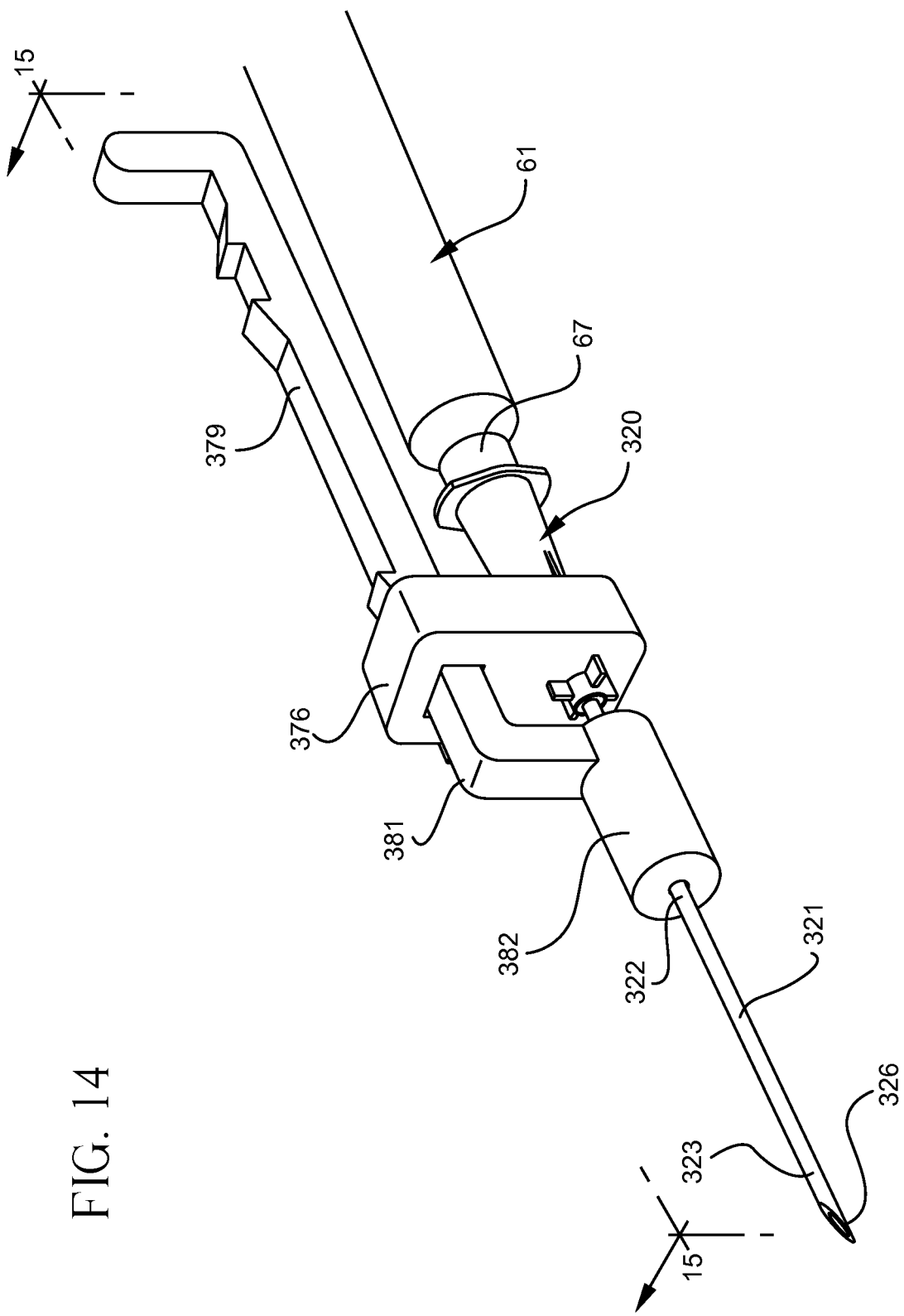
FIG. 14 is a side-elevational view of an alternative embodiment of the needle assembly of the present invention illustrated after frictional engagement with a syringe barrel tip.
Figure 15:
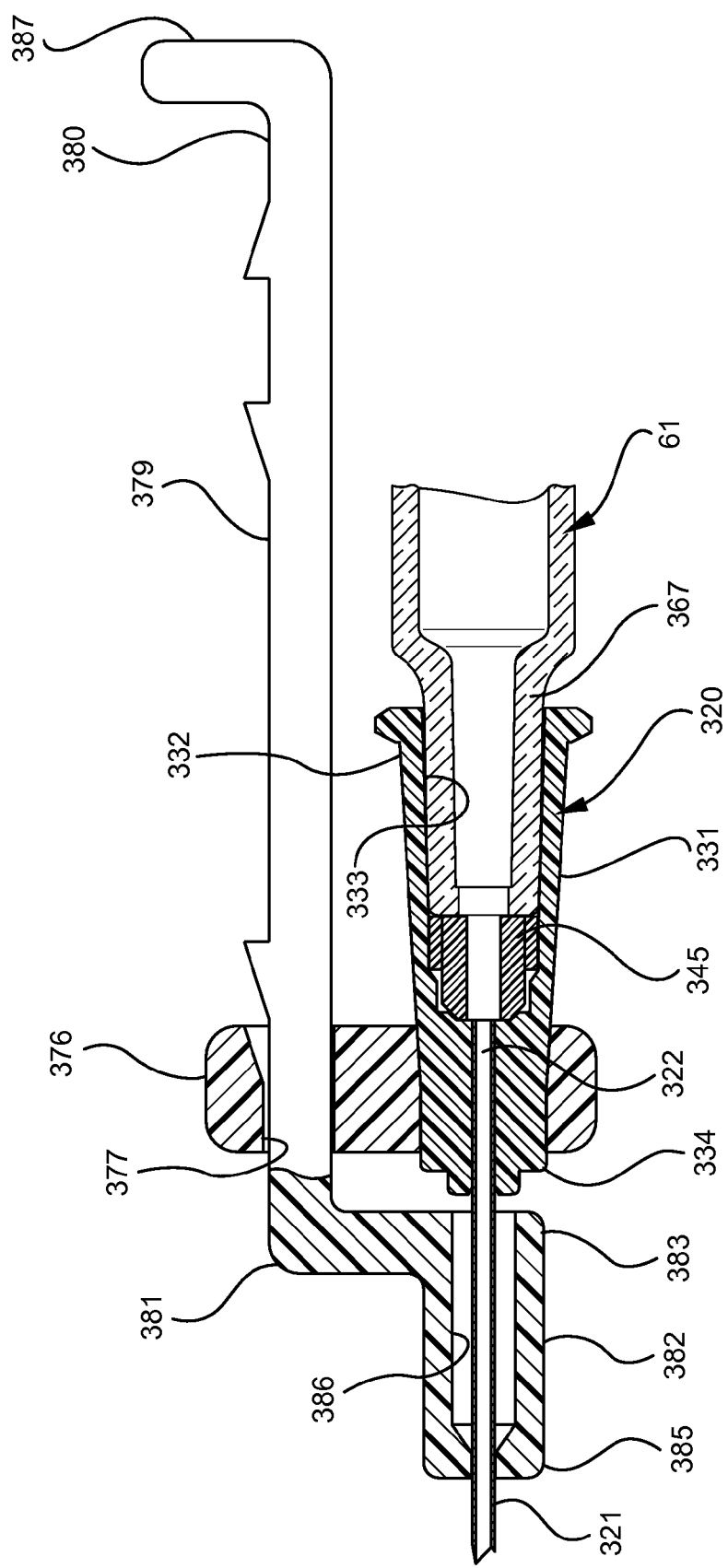
FIG. 15 is a cross-sectional view of the needle assembly and syringe barrel of FIG. 14 taken along line 15-15.

FIGS. 14 and 15 illustrate another alternative embodiment of the medical device of the present invention. In this embodiment, needle assembly 320 includes a needle cannula 321 having a proximal end 322, a distal end 323 and a lumen therethrough. A hub 331 includes an open proximal end 332 with a frusto-conically-shaped cavity 333 therein, a distal end 334 and a passageway therethrough. The cavity is part of the passageway. The proximal end of the needle cannula is joined to the distal end of the hub so that the lumen is in fluid communication with the passageway. A release element 345 is in the passageway of the hub positioned to block fluid-tight engagement of frusto-conically shaped tip 367 of syringe barrel 61 with the cavity of the hub until all or part of the release element is displaced distally in the passageway by action of force applied to the release element by the distal end of the syringe barrel tip as illustrated in FIG. 15. Release element 345 functions in a similar manner as release element 245 in the embodiment of FIGS. 10-13. Hub 331 further includes a guide element 376 having an aperture 377 therethrough. An elongate barrier arm 379 having a proximal end 380 and a distal end 381 includes a barrier element 382 on distal end 381. The barrier element includes a proximal end 383, a distal end 385 and a needle passageway 386 therethrough. The barrier arm is positioned within the aperture of the guide element and the needle cannula is positioned at least partially within the needle passageway of the barrier element. The barrier element is movable from at least a first retracted position, illustrated in FIGS. 14-15, wherein the distal end of the needle cannula passes completely through the barrier element so that the distal end of the needle cannula is exposed, to a second extended position (not illustrated) wherein the barrier element surrounds the distal end of the needle cannula to prevent incidental contact with tip 326 on the distal end of the needle cannula. A finger contact surface 387 on the barrier arm is provided for applying digital force to the barrier arm to move the barrier arm into the second extended position. This is accomplished by applying a digital force to the finger contact surface having at least a component in direction B as illustrated in FIG. 14. The aperture in the guide element can be any shape, closed or open, which works cooperatively to guide the barrier arm between the first retracted position and the second extended position. The barrier arm may be curved or the aperture in the guide element angled so that the needle passageway misaligns with tip 326 on the needle cannula to help prevent movement of the barrier element from the second extended position.

Figure 16:
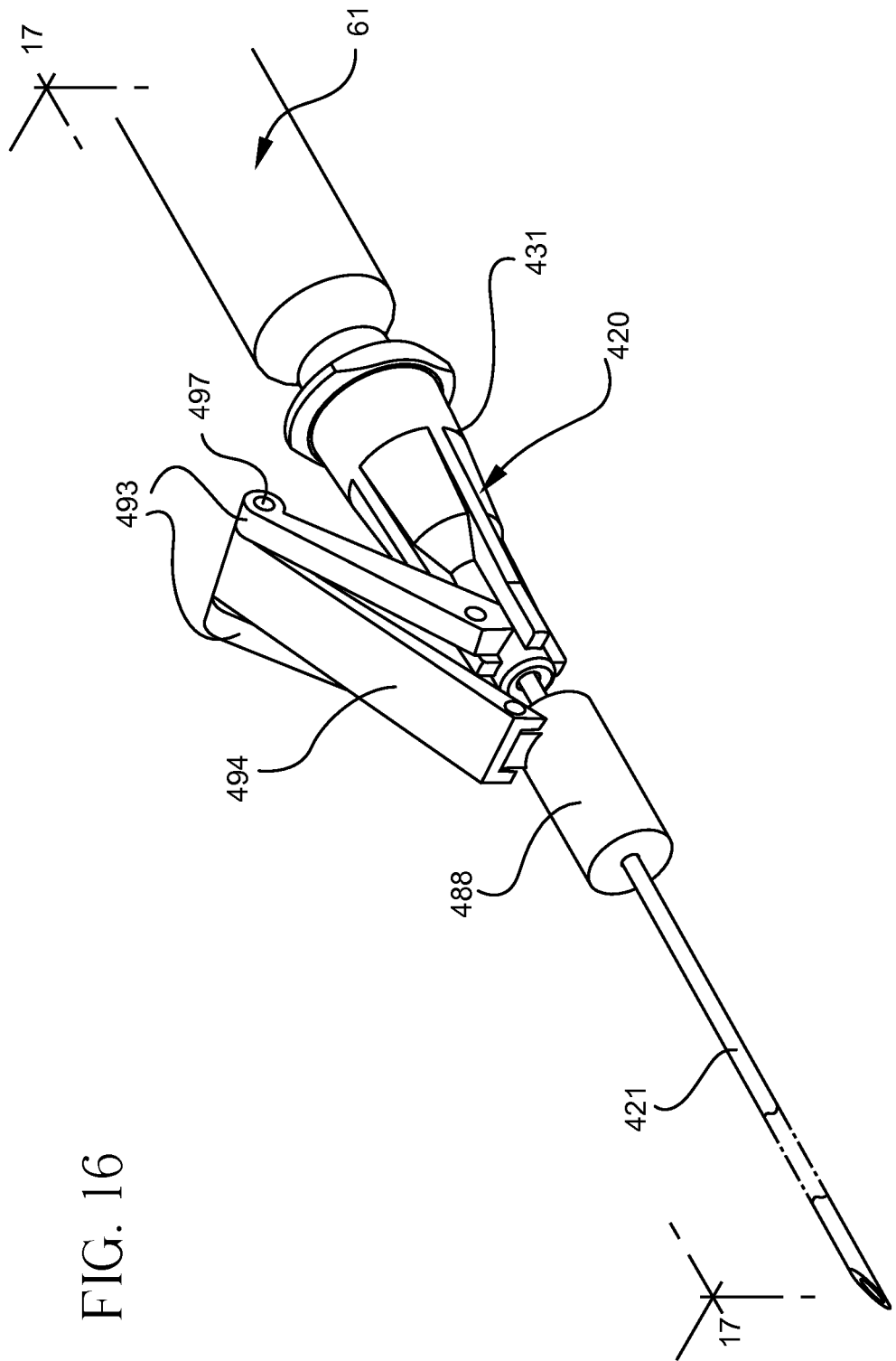
FIG. 16 is side-elevational view of another alternative embodiment of the needle assembly of the present invention illustrated after frictional engagement with a syringe barrel tip.
Figure 17:
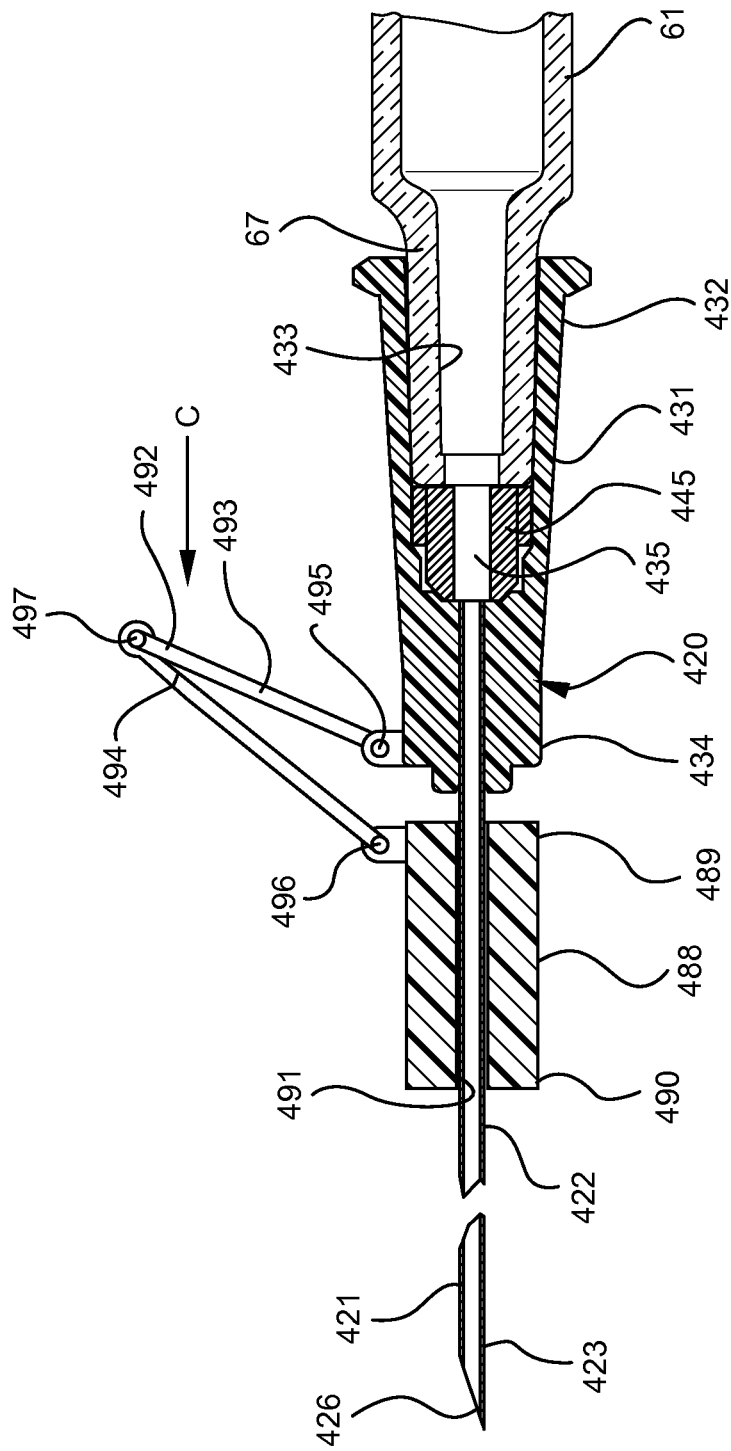
FIG. 17 is a cross-sectional view of the needle assembly and syringe barrel of FIG. 16 taken along line 17-17.

FIGS. 16-17 illustrate another alternative embodiment of the needle assembly of the present invention. In this embodiment, needle assembly 420 includes a needle cannula 421 having a proximal end 422, a distal end 423 and a hub 431. Hub 431 includes an open proximal end 432 with a frusto-conically shaped cavity 433, a distal end 434 and a passageway 435 therethrough. The cavity is part of the passageway. The proximal end of the needle cannula is joined to the distal end of the hub so that the lumen of the needle cannula is in fluid communication with the passageway. A release element 445 is in the passageway of the hub positioned to block fluid-tight engagement of a frusto-conically shaped tip such as tip 67 on syringe barrel 61 with the cavity of the hub until all or part of the release element is displaced distally in the passageway by action of force applied to the release element by the distal end of the syringe barrel tip as illustrated in FIG. 17. Release element 445 functions in a similar manner to the release element 245 in FIGS. 10-13. Needle assembly 420 further includes a needle guard 488 having a proximal end 489, a distal end 490 and a needle passageway 491 therethrough. The needle guard is movable along the needle cannula from a first position substantially adjacent to the proximal end of the needle cannula, as illustrated in FIGS. 16-17, to a second position where a distal tip 426 of needle cannula is intermediate the opposed proximal and distal ends of needle guard 488. A hinged arm 492 having a proximal segment 493 and a distal segment 494 which are articulated to one another for movement between a first position where the segments are substantially collapsed onto one another, as illustrated in FIGS. 16-17, and a second position where the segments are extended from one another. The proximal segment of the hinged arm is articulated to a portion of the hub through a structure that allows such movement, such as hinge 495 in this embodiment. The distal segment of the hinged arm is articulated to needle guard 488 through hinge 496. Proximal segment 493 and distal segment 494 are articulated with respect to each other through hinge 497. The proximal and distal segments of the hinged arm have respective lengths for permitting the needle guard to move from the first position to the second position on the needle cannula and for preventing the guard from moving distally beyond the second position. The needle guard is moved to the second position through the application of a digital force having at least a component in direction C as illustrated in FIG. 17. The hinges may be mechanical hinges or linkages or flexible connections such as living hinges.

Figure 18:
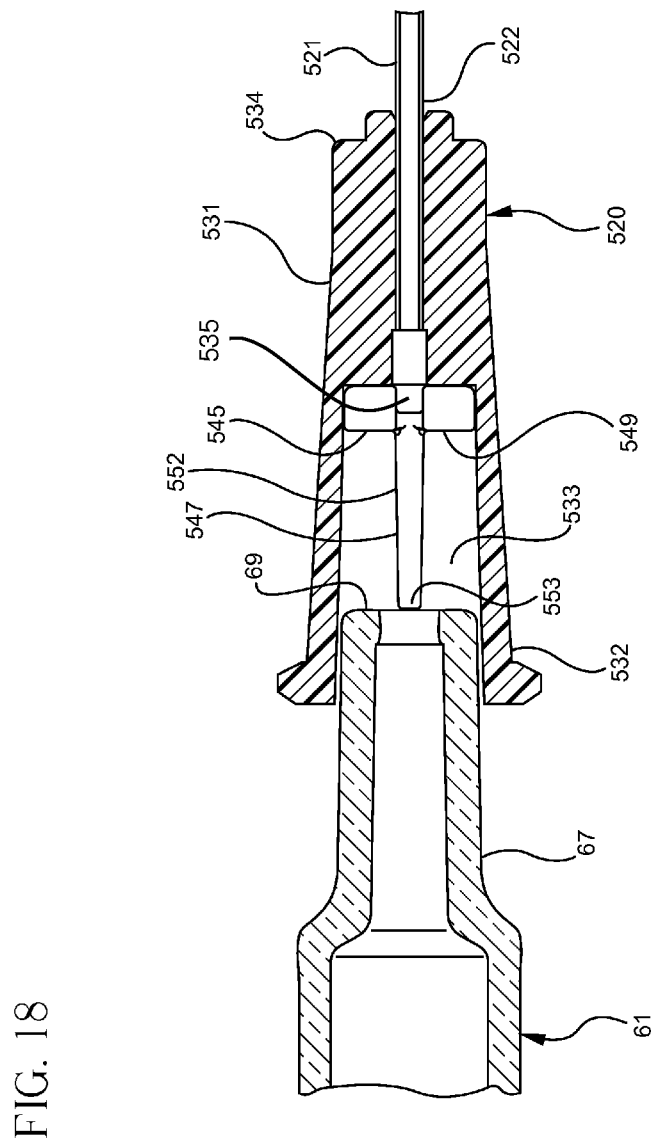
FIG. 18 is a partial cross-sectional view of another alternative embodiment of the needle assembly of the present invention illustrated before frictional engagement with a syringe barrel tip.
Figure 19:
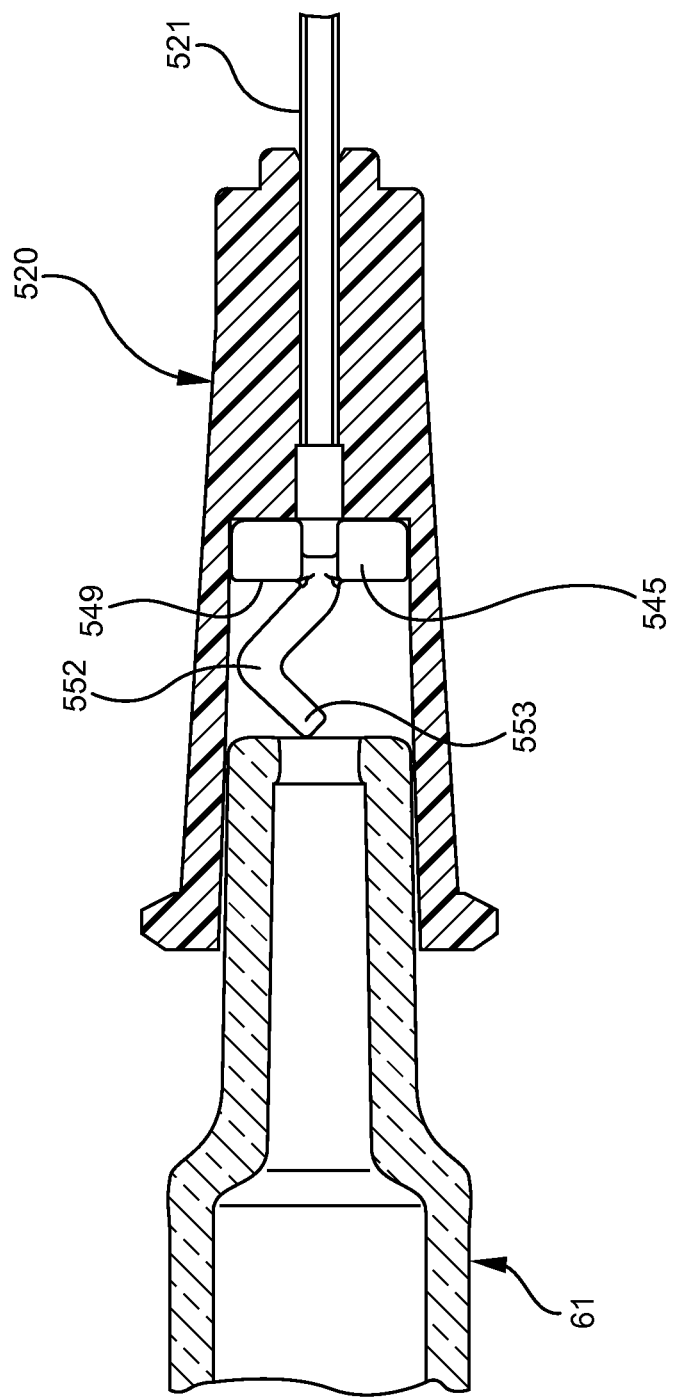
FIGS. 19 and 20 illustrate the needle assembly of FIG. 18 after frictional engagement with a syringe barrel tip.
Figure 20:
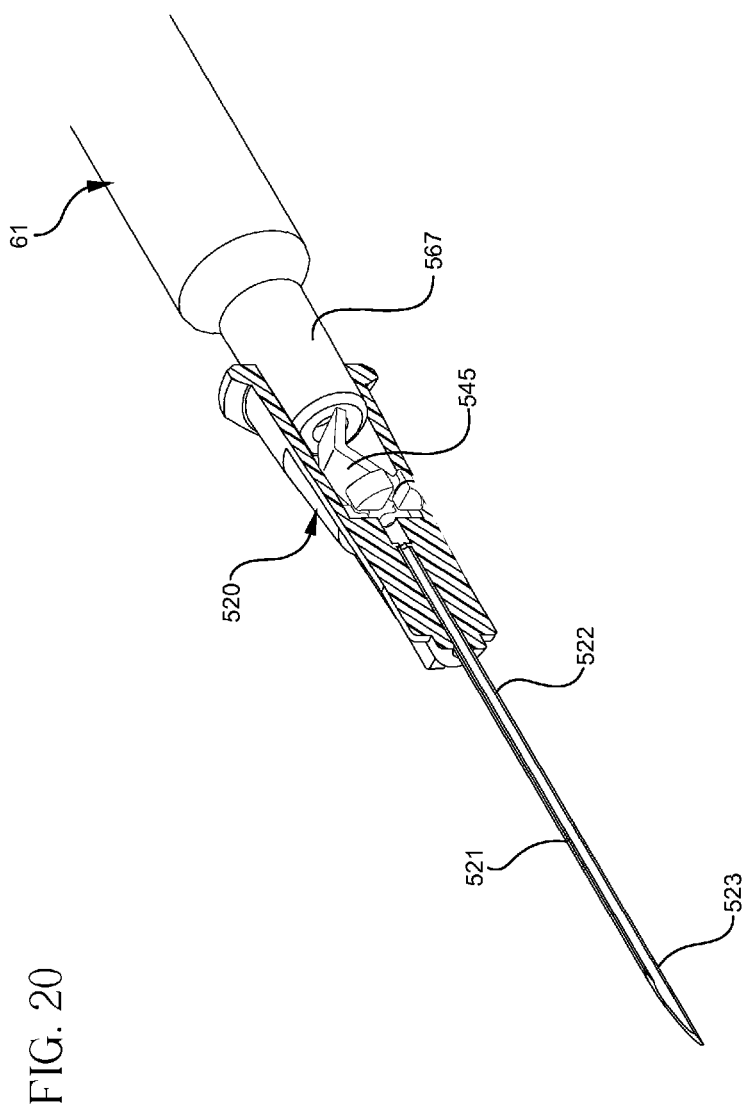

FIGS. 18-20 illustrate another alternative embodiment of the medical device of the present invention. In this embodiment, needle assembly 520 includes a needle cannula 521 having a proximal end 522, a distal end and a lumen therethrough. A hub 531 includes an open proximal end 532 with a frusto-conically shaped cavity 533 therein, a distal end 534 and a passageway 535 therethrough. The cavity is part of the passageway. The proximal end of the needle cannula is joined to the distal end of the hub so that the lumen is in fluid communication with the passageway. A release element 545, in the passageway, is positioned to block fluid-tight engagement of frusto-conically shaped tip 567 of syringe barrel 61 with cavity 533 of hub 531. In this embodiment, release element 545 includes distal end 549 positioned in the passageway and proximal end 547 which includes proximally directed axial beam 552. The axial beam includes a free end 553 adapted to contact distal end 69 of the barrel tip to block fluid-tight engagement of the tip and the hub. In this embodiment means for releasing includes the axial beam being configured to buckle upon application of a pre-determined proximally-directed force as best illustrated in FIGS. 15 and 16. Axial beam 552 preferably has a rectangularly-shaped cross section. The distal end of the release element also includes at least one channel and preferably a plurality of channels 545 for accepting liquid flow from a syringe barrel through the passageway. A wide variety of materials can be used to produce a buckling beam with thermoplastic being preferred. It is also preferred that the entire release element 545 be integrally formed of the same material, preferably thermoplastic. Also, it is desirable to have the release element and the hub integrally formed of the same material, preferably thermoplastic.

Figure 21:
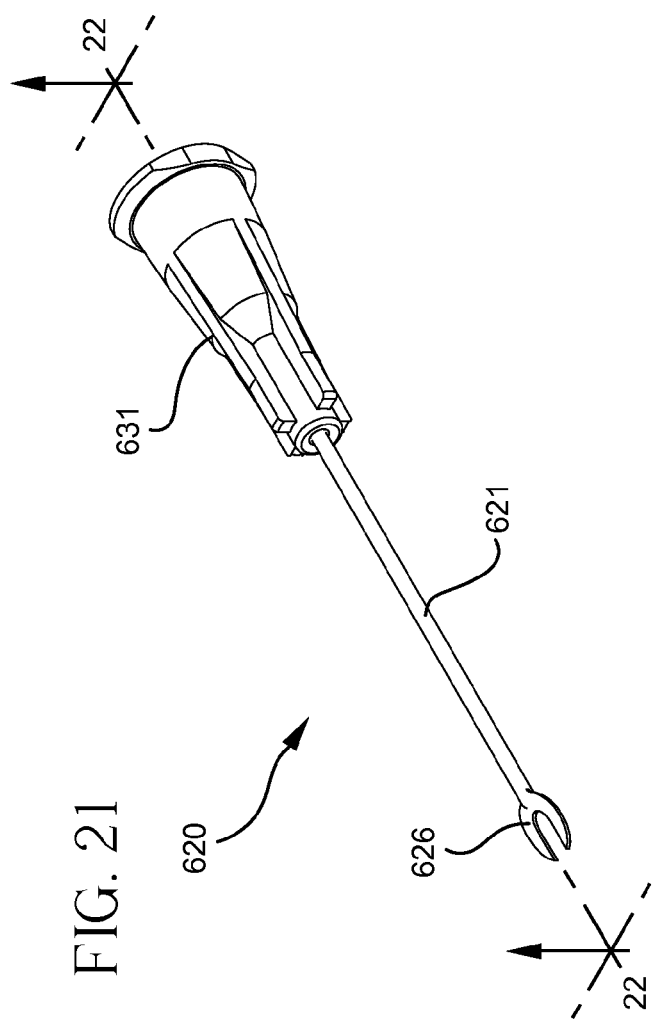
FIG. 21 is a perspective view of another alternative needle assembly of the present invention.
Figure 22:
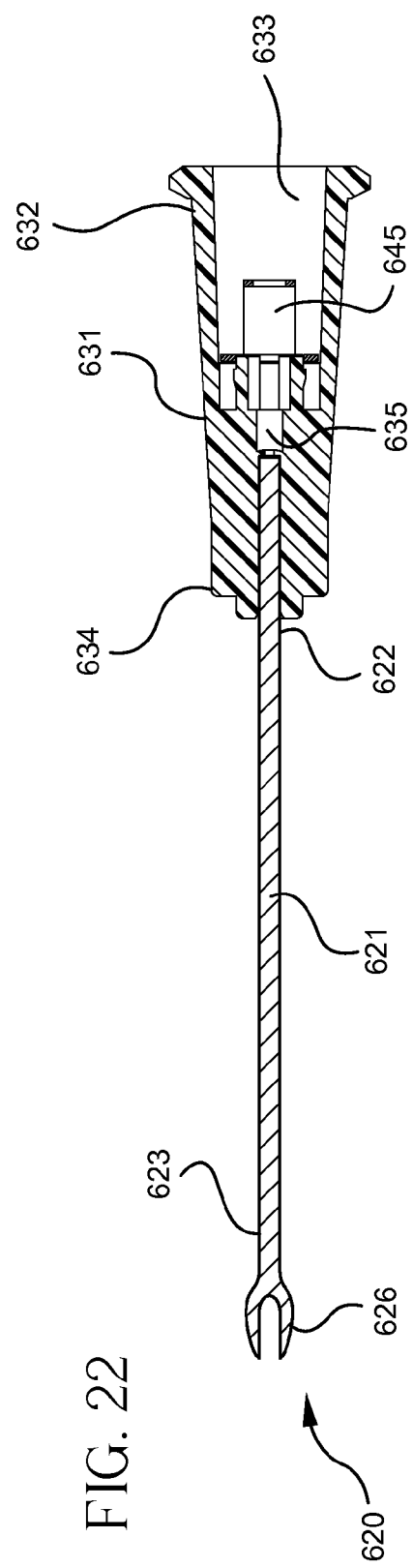
FIG. 22 is an enlarged cross-sectional view of the needle assembly of FIG. 21 taken along line 21-21.

FIGS. 21 and 22 illustrate another embodiment of the needle assembly of the present invention. In this embodiment, needle assembly 620 includes a needle 621 having a proximal end 622, a distal end 623 and a hub 631. Hub 631 includes an open proximal end 632 with a frusto-conically shaped cavity 633, a distal end 634 and a passageway 635 therethrough. The cavity is part of the passageway. The proximal end of the needle is jointed to the distal end of the hub so that the needle projects distally outwardly from the distal end of the hub. A release element 645 is in the passageway of the hub positioned to block fluid-tight engagement of the frusto-conically shaped tip of a medical device such as a syringe barrel with the cavity of the hub until all or part of the release element is displaced distally in the passageway by action of force applied to the release element by the distal end of the syringe barrel tip. Release element 645 functions in a similar manner as release element 45 in the embodiment of FIGS. 1-7. Needle 621 does not have a functioning lumen and in this embodiment has a bifurcated distal tip 626. Solid needles such as the needle having a bifurcated tip are commonly used for administering vaccines, antigens and other substances to the skin. The bifurcated tip is used to scratch or slightly pierce the skin of the patient so that the liquid substance, such as a vaccine, may be absorbed into the skin of the patient. The needle assembly of this embodiment can be attached to a syringe barrel, wherein the syringe barrel is used as a handle to control and guide the needle tip during the vaccination process.

What is claimed is:

1. A medical device for use with a fluid transfer device having a frusto-conically shaped tip comprising:
   a hub having an open proximal end with a frusto-conically shaped cavity therein, a distal end and a passageway therethrough, said cavity being part of said passageway; and
   a release element in said passageway of said hub positioned to block fluid-tight engagement of said frusto-conically shaped tip with said cavity of said hub, said release element including a distal end in said passageway including a plurality of channels for accepting liquid flow from said fluid transfer device through said passageway and a proximal end including a proximally directed axial beam, said beam having a free end adapted to contact the distal end of said frusto-conically shaped tip to block fluid-tight engagement of said tip and said hub;
   wherein said beam buckles upon application of a proximally directed force on said hub, to allow abrupt fluid-tight engagement of said tip and said cavity in said hub.

2. The medical device of claim 1 wherein said beam has a rectangularly shaped cross-section.

3. The needle assembly of claim 1 wherein said release element is made of thermoplastic material.

4. The needle assembly of claim 1 wherein said release element and said hub are integrally formed of thermoplastic material.

5. The medical device of claim 1 wherein said hub is made of thermoplastic material.

6. The medical device of claim 5 wherein said thermoplastic material consists of materials selected from the group of polypropylene, polyethylene, polycarbonate and combinations thereof.

7. The medical device of claim 1 further including a needle cannula having a proximal end, a distal end and a lumen therethrough, said proximal end of said needle cannula being joined to said distal end of said hub so that said lumen is in fluid communication with said passageway.

8. The medical device of claim 7 wherein said hub includes a pivotable needle shield having a cavity therein hingedly connected to said hub and capable of pivoting from a needle exposing position which allows access to said distal end of said needle cannula and a needle protecting position wherein said distal end of said needle cannula is within the cavity of said needle shield.

9. The medical device of claim 7 further comprising:
a guide element on said hub having an aperture therethrough;
an elongate barrier arm having a proximal end and a distal end, said distal end of said barrier arm including a barrier element having a distal end, a proximal end and a needle passageway therethrough, said barrier arm positioned within said aperture of said guide element and said needle cannula positioned at least partially within said needle passageway of said barrier element, said barrier arm being movable from at least a first retracted position wherein said distal end of said needle cannula passes completely through said barrier element so that said distal end of said needle cannula is exposed, to a second extended position wherein said barrier element surrounds said distal end of said needle cannula to prevent incidental contact with said distal end of said needle cannula; and
a finger contact surface on said barrier arm for applying digital force to said barrier arm to move said barrier arm into said second extended position.

10. The medical device of claim 7 further comprising:
a needle guard having a proximal end, a distal end and a needle passageway therethrough, said needle guard being movable along said needle cannula from a first position substantially adjacent said proximal end of said needle cannula to a second position where said distal end of said needle cannula is intermediate said opposed proximal and distal ends of said needle guard;
a hinged arm having proximal and distal segments articulated to one another for movement between a first position where said segments are substantially collapsed onto one another and a second position where said segments are extended from one another, said proximal segment of said hinged arm being articulated to a portion of said hub, said distal segment of said hinged arm being articulated to said guard, said proximal and distal segments of said hinged arm having respective lengths for permitting said guard to move from said first position to said second position on said needle cannula, and for preventing said guard from moving distally beyond said second position.

11. The medical device of claim 10 wherein said needle guard, said proximal segment and said distal segment are integrally formed of thermoplastic material.

12. The medical device of claim 1 further including an elongate needle having a proximal end and a distal end, said proximal end of said needle being joined to said distal end of said hub.

13. The medical device of claim 1 further including a syringe barrel having an inside surface defining a chamber, an open proximal end and a distal end including an elongate frusto-conically shaped tip having a conduit therethrough, said medical device being connected to said syringe barrel so that said frusto-conically shaped tip is in fluid-tight engagement with said frusto-conically shaped cavity of said hub and said passageway is in fluid communication with said chamber of said syringe barrel.

14. The medical device of claim 1 wherein said proximally directed force is equal or greater than 0.5 kg.

15. The medical device of claim 1 wherein said proximally directed force is between 1 kg. and 5 kg.

16. The medical device of claim 1 wherein the hub and the release element are configured to provide an audible indication of said abrupt fluid-tight engagement of said tip and said cavity.

17. A medical device for use with a fluid transfer device having a frusto-conically-shaped tip comprising:
a needle cannula having a proximal end, a distal end and a lumen therethrough; a hub having an open proximal end with a frusto-conically shaped cavity therein, a distal end and a passageway therethrough, said cavity being part of said passageway, said proximal end of said needle cannula being joined to said distal end of said hub so that said lumen is in fluid communication with said passageway;
a release element in said passageway of said hub positioned to block fluid-tight engagement of said frusto-conically shaped tip with said cavity of said hub, said release element including a distal end in said passageway including a plurality of channels for accepting liquid flow from said fluid transfer device through said passageway and a proximal end including a proximally directed axial beam, said beam having a free end adapted to contact the distal end of said frusto-conically shaped tip to block fluid-tight engagement of said tip and said hub;
wherein said beam buckles upon application of a proximally directed force of equal or greater than 0.5 kg on said hub, to allow abrupt fluid-tight engagement of said tip and said cavity in said hub.

* * * * *